(12) United States Patent
Bogdan et al.

(10) Patent No.: US 9,309,170 B2
(45) Date of Patent: Apr. 12, 2016

(54) AROMATICS ISOMERIZATION USING A DUAL-CATALYST SYSTEM

(71) Applicant: UOP LLC, Des Plaines, IL (US)

(72) Inventors: Paula L. Bogdan, Mount Prospect, IL (US); James A. Johnson, Burr Ridge, IL (US); Gregory J. Gajda, Mount Prospect, IL (US); Patrick C. Whitchurch, Sleepy Hollow, IL (US); Stanley J. Frey, Palatine, IL (US); Wolfgang A. Spieker, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 57 days.

(21) Appl. No.: 13/649,546

(22) Filed: Oct. 11, 2012

(65) Prior Publication Data

US 2013/0123558 A1    May 16, 2013

Related U.S. Application Data

(60) Provisional application No. 61/559,226, filed on Nov. 14, 2011.

(51) Int. Cl.
  *C07C 5/29* (2006.01)
  *C07C 5/27* (2006.01)

(52) U.S. Cl.
  CPC ........... *C07C 5/2708* (2013.01); *C07C 2521/02* (2013.01); *C07C 2521/04* (2013.01); *C07C 2521/06* (2013.01); *C07C 2521/08* (2013.01); *C07C 2521/12* (2013.01); *C07C 2521/16* (2013.01); *C07C 2523/02* (2013.01); *C07C 2523/06* (2013.01); *C07C 2523/08* (2013.01); *C07C 2523/10* (2013.01); *C07C 2523/12* (2013.01); *C07C 2523/14* (2013.01); *C07C 2523/26* (2013.01); *C07C 2523/30* (2013.01); *C07C 2523/36* (2013.01); *C07C 2523/42* (2013.01); *C07C 2523/44* (2013.01); *C07C 2523/46* (2013.01); *C07C 2523/745* (2013.01); *C07C 2523/75* (2013.01); *C07C 2523/755* (2013.01); *C07C 2527/224* (2013.01); *C07C 2529/89* (2013.01)

(58) Field of Classification Search
  CPC ...... C07C 5/2737; C07C 5/2775; C07C 15/08
  USPC .................................................. 585/481, 482
  See application file for complete search history.

(56) References Cited

U.S. PATENT DOCUMENTS

| | | | |
|---|---|---|---|
| 3,856,872 A | 12/1974 | Morrison | |
| 4,899,011 A * | 2/1990 | Chu et al. | 585/481 |
| 6,512,155 B1 | 1/2003 | Johnson | |
| 7,297,830 B2 | 11/2007 | Bogdan | |
| 7,525,008 B2 | 4/2009 | Bogdan | |
| 2005/0059847 A1 * | 3/2005 | Stern | 585/481 |
| 2008/0183023 A1 | 7/2008 | Zhou | |

OTHER PUBLICATIONS

PCT International Preliminary Report on Patentability for PCT/US2012/061880, Applicant Reference H0020391-01.

* cited by examiner

*Primary Examiner* — Thuan D Dang

(57) ABSTRACT

This invention is drawn to a process for isomerizing a non-equilibrium mixture of xylenes and ethylbenzene which contain a substantial concentration of nonaromatics using a catalyst system which features the ability to both convert nonaromatics and to obtain an improved yield of para-xylene from the mixture relative to processes of the known art.

14 Claims, No Drawings

AROMATICS ISOMERIZATION USING A DUAL-CATALYST SYSTEM

CROSS-REFERENCE TO RELATED APPLICATION

This application claims benefit of U.S. Provisional Application No. 61/559,226 which was filed on Nov. 14, 2011.

FIELD OF THE INVENTION

This invention relates to catalytic hydrocarbon conversion, and more specifically to the use of an improved molecular-sieve catalyst system in aromatics isomerization.

GENERAL BACKGROUND AND RELATED ART

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Para-xylene in particular is a major chemical intermediate with rapidly growing demand, but amounts to only 20-25% of a typical $C_8$ aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

Various catalysts and processes have been developed to effect xylene isomerization. In selecting appropriate technology, it is desirable to run the isomerization process as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e. very close approach to equilibrium) and high utility costs due to the large recycle rate of unconverted $C_8$ aromatics. Catalysts thus are evaluated on the basis of a favorable balance of activity, selectivity and stability.

Catalysts containing molecular sieves have become prominent for xylene isomerization in recent decades. U.S. Pat. No. 3,856,872 for example, teaches xylene isomerization and ethylbenzene conversion with a catalyst containing ZSM-5, -12, or -21 zeolite. U.S. Pat. No. 4,899,011 teaches isomerization of $C_8$ aromatics using two zeolites, each of which is associated with a strong hydrogenation metal. U.S. Pat. No. 6,142,941; U.S. Pat. No. 7,297,830 B2; and U.S. Pat. No. 7,525,008 B2 disclose zeolitic catalysts useful in isomerization of $C_8$ aromatics and are incorporated herein by reference thereto. Although these references teach individual elements of the present invention, none of the art suggests combination of the elements to obtain the critical features of the catalyst system of the present invention.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion and more effective xylene isomerization, thus lowering the quantity of recycle in a loop of isomerization/para-xylene recovery and reducing concomitant processing costs.

SUMMARY OF THE INVENTION

A principal object of the present invention is to provide a novel catalyst and process for the isomerization of alkylaromatic hydrocarbons. More specifically, this invention is directed to a catalyst system for isomerization of $C_8$ aromatic hydrocarbons which contain substantial concentrations of nonaromatics to yield a high-purity product.

Accordingly, a broad embodiment of the invention is directed toward process for the conversion of a hydrocarbon feed mixture comprising a major concentration of nonequilibrium $C_8$ aromatics and a minor concentration of nonaromatics by contacting the mixture with a dual-catalyst system comprising a first catalyst comprising one or both of a tungsten component and at least one zeolitic aluminosilicate and a second catalyst comprising from about 0.01 to about 0.2 mass-% on an elemental basis of at least one platinum-group metal component at hydrocarbon-conversion conditions comprising a temperature of about 300° to about 550° C., a pressure of about 100 kPa to 5 MPa and a liquid hourly space velocity of about 0.5 to 50 $hr^{-1}$ with respect to the dual-catalyst system to obtain a converted product comprising a reduced concentration of ethylbenzene and a reduced concentration of nonaromatics than in the feed mixture.

In one embodiment, the invention comprises a process for the conversion of a hydrocarbon feed mixture comprising a major concentration of nonequilibrium $C_8$ aromatics and a minor concentration of nonaromatics by contacting the mixture with a dual-catalyst system comprising a first catalyst comprising from about 10 to about 99 mass-% of at least one zeolitic aluminosilicate and a second catalyst comprising from about 0.01 to about 0.2 mass-% on an elemental basis of at least one platinum-group metal component at hydrocarbon-conversion conditions comprising a temperature of about 300° to about 550° C., a pressure of about 100 kPa to 5 MPa and a liquid hourly space velocity of about 0.5 to 50 $hr^{-1}$ with respect to the dual-catalyst system to obtain a converted product comprising a higher proportion of at least one xylene isomer, a reduced concentration of ethylbenzene and a reduced concentration of nonaromatics than in the feed mixture.

In an alternative embodiment, the invention comprises a process for the conversion of a hydrocarbon feed mixture comprising a major concentration of nonequilibrium $C_8$ aromatics and a minor concentration of nonaromatics by contacting the mixture with a dual-catalyst system comprising a first catalyst comprising a tungsten component and a second catalyst comprising from about 0.01 to about 0.2 mass-% on an elemental basis of at least one platinum-group metal component at hydrocarbon-conversion conditions comprising a temperature of about 300° to about 550° C., a pressure of about 100 kPa to 5 MPa and a liquid hourly space velocity of about 0.5 to 50 $hr^{-1}$ with respect to the dual-catalyst system to obtain a converted product comprising a reduced concentration of ethylbenzene and a reduced concentration of nonaromatics than in the feed mixture.

These as well as other objects and embodiments will become evident from the following detailed description of the invention.

DETAILED DESCRIPTION OF THE INVENTION

The feedstock to aromatics isomerization comprises isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including al the isomers thereof to obtain more valuable isomers of the alkylaromatic. Suitable alkylaromatic hydrocarbons include, for example but without so limiting the invention, ortho-xylene, meta-xylene, para-xylene, ethylbenzene, ethyltoluenes, tri-methylbenzenes, di-ethylbenzenes, tri-ethyl-benzenes, methylpropylbenzenes, ethylpropylbenzenes, di-isopropylbenzenes, and mixtures thereof.

Isomerization of a $C_8$ aromatic mixture containing ethylbenzene and xylenes is a particularly preferred application of the catalyst system of the invention. Generally such mixture will have an ethylbenzene content in the approximate range of 1 to 50 mass-%, an ortho-xylene content in the approximate range of 0 to 35 mass-%, a meta-xylene content in the approximate range of 20 to 95 mass-% and a para-xylene content in the approximate range of 0 to 30 mass-%. It is preferred that the aforementioned $C_8$ aromatics comprise a non-equilibrium mixture, i.e., at least one $C_8$ aromatic isomer is present in a concentration that differs substantially from the equilibrium concentration at isomerization conditions. Usually the non-equilibrium mixture is prepared by removal of para-, ortho- and/or meta-xylene from a fresh $C_8$ aromatic mixture obtained from an aromatics-production process.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A C8 aromatics feed to the present process may contain nonaromatic hydrocarbons, i.e., naphthenes and paraffins, in an amount up to 30 mass-%. The present invention is particularly useful for the processing of feedstocks containing concentration of nonaromatics that would be troublesome in other processes.

According to the process of the present invention, an alkylaromatic hydrocarbon feed mixture, preferably in admixture with hydrogen, is contacted with two or more catalysts of the type hereinafter described in an alkylaromatic-hydrocarbon isomerization zone. Contacting may be effected using the catalyst system in a fixed-bed system, a moving-bed system, a fluidized-bed system, slurry system or ebullated-bed system or in a batch-type operation. In view of the danger of attrition loss of valuable catalysts and of the simpler operation, it is preferred to use a fixed-bed system. In this system, a hydrogen-rich gas and the feed mixture are preheated by suitable heating means to the desired reaction temperature and then passed into an isomerization zone containing a fixed bed or beds of two or more catalysts. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The first and second catalysts may be contained in separate reactors, arranged sequentially in the same reactor, mixed physically, or composited as a single catalyst. Preferably the catalysts are arranged in sequence, with the feed contacting the first catalyst to convert nonaromatics to yield an intermediate stream for processing by the second catalyst to convert ethylbenzene and isomerize aromatics to yield an isomerized product.

Location of the catalysts in separate reactors permits independent control of operating conditions, particularly temperature and space velocity. By employing a single reactor, however, savings are realized in piping, instrumentation and other appurtenances. Physical mixing of the catalysts would facilitate synergistic reactions of the catalysts, but separation and recovery of catalyst components would be more difficult. The system of catalysts optionally may be repeated in one or more additional stages, i.e., reactants from the contacting of the feed are processed in another sequence of the two catalysts.

In an alternative embodiment of the invention, therefore, the reactor contains a physical mixture of the first and second catalyst. In this embodiment, particles are mechanically mixed to provide the catalyst system of the invention. The particles can be thoroughly mixed using known techniques such as mulling to intimately blend the physical mixture. Although the first and second particles may be of similar size and shape, the particles preferably are of different size and/or density for ease of separation for purposes of regeneration or rejuvenation following their use in hydrocarbon processing.

As yet another alternative embodiment of the present invention, a physical mixture of the first and second catalysts is contained within the same catalyst particle. In this embodiment, the sieves may be ground or milled together or separately to form particles of suitable size, preferably less than 100 microns, and the particles are supported in a suitable matrix. Optimally the matrix is selected from the inorganic oxides described hereinabove.

The alkylaromatic feed mixture, preferably a non-equilibrium mixture of $C_8$ aromatics, is contacted with the catalyst system at suitable alkylaromatic-conversion conditions. Such conditions comprise a temperature ranging from about 100° to 600° C. or more, and preferably in the range of about 300° to 550° C. The pressure generally is from about 100 kPa to 5 MPa absolute, preferably less than about 3 MPa. A sufficient volume of both catalysts comprising the catalyst system is contained in the isomerization zone to provide a liquid hourly space velocity with respect to the hydrocarbon feed mixture of about 0.5 to 50 $hr^{-1}$, and preferably 0.5 to 25 $hr^{-1}$ with respect to each of the catalysts comprising the catalyst system, the space velocity is within the range of about 1 to 100 $hr^{-1}$. The hydrocarbon feed mixture optimally is reacted in admixture with hydrogen at a hydrogen/hydrocarbon mole ratio of about 0.5:1 to 25:1. Other inert diluents such as nitrogen, argon and light hydrocarbons may be present. If the two or more catalysts are contained in separate beds, different operating conditions within the above constraints may be used within each of the beds in order to achieve optimum overall results.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described U.S. Pat. No. 3,626,020; U.S. Pat. No. 3,696,107; U.S. Pat. No. 4,039,599; U.S. Pat. No. 4,184,943; U.S. Pat. No. 4,381,419 and U.S. Pat. No. 4,402,832, incorporated herein by reference thereto.

In a separation/isomerization process combination relating to the processing of an ethylbenzene/xylene mixture, a fresh $C_8$ aromatic feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$ aromatic isomers are isomerized to near-equilibrium levels to obtain the isomerized product. In this process scheme non-recovered $C_8$ aromatic isomers preferably are recycled to extinction until they are either converted to para-xylene or lost due to side-reactions. Ortho-xylene separation, preferably by fractionation, also may be effected on the fresh $C_8$ aromatic feed or isomerized product, or both in combination, prior to para-xylene separation.

The second catalyst may be a catalyst of the known art suitable for conversion of ethylbenzene and isomerization of xylenes. A preferred catalyst is a spherical catalyst comprising a zeolitic aluminosilicate, platinum-group metal component and amorphous aluminum phosphate binder as disclosed in U.S. Pat. No. 6,143,941. Conversion by the first catalyst of nonaromatics contained in the feedstock enables the use of such catalysts.

The mass ratio of first catalyst to second catalyst depends primarily on the feedstock composition and desired product distribution, with a first:second catalyst mass ratio of about 1:20 to 50:1 being preferred and from about 1:10 to 20:1 being especially preferred. The catalyst system of the invention may include other catalysts, either sieve-based or amorphous.

The relative proportion of zeolite, when present in the first and second catalyst may range from about 10 to about 99 mass-%, with about 20 to about 90 mass-% being preferred.

A binder should be a porous, adsorptive support having a surface area of about 25 to about 500 m$^2$/g, uniform in composition and relatively refractory to the conditions utilized in the hydrocarbon conversion process. By the term "uniform in composition," it is meant that the support is unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in hydrocarbon conversion catalysts such as: (1) refractory inorganic oxides such as alumina, titania, zirconia, chromia, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO—Al_2O_3$ where M is a metal having a valence of 2; and (6) combinations of materials from one or more of these groups.

A preferred refractory inorganic oxide for use in the present invention is alumina. Suitable alumina materials are the crystalline aluminas known as the gamma-, eta-, and theta-alumina, with gamma- or eta-alumina giving best results. Desirably, the inorganic oxide is an alumina, such as a gamma-alumina. Such a gamma-alumina can be derived from a boehmite or a pseudoboehmite alumina (hereinafter collectively may be referred to as "boehmite alumina"). The boehmite alumina can be compounded with the zeolite and extruded. During oxidation (or calcination), the boehmite alumina may be converted into gamma-alumina. One desired boehmite alumina utilized as a starting material is VERSAL-251 sold by UOP, LLC of Des Plaines, Ill. Another boehmite alumina can be sold under the trade designation CATAPAL C by Sasol North America of Houston, Tex. Generally, preparation of alumina-bound spheres involves dropping a mixture of molecular sieve, aluminum sol, and gelling agent into an oil bath maintained at elevated temperatures. Examples of gelling agents that may be used in this process include hexamethylene tetraamine, urea, and mixtures thereof. The gelling agents can release ammonia at the elevated temperatures which sets or converts the hydrosol spheres into hydrogel spheres. The spheres may then be withdrawn from the oil bath and typically subjected to specific aging treatments in oil and an ammonia solution to further improve their physical characteristics. One exemplary oil dropping method is disclosed in U.S. Pat. No. 2,620,314.

An alternative binder is a form of amorphous silica. The favored amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 120 to 160 m$^2$/g. A low content of sulfate salts is desired, preferably less than 0.3 wt-%. It is especially preferred that the amorphous silica binder be nonacidic, e.g., that the pH of a 5% water suspension be neutral or basic (pH about 7 or above).

A preferred shape of the composite is a sphere continuously manufactured by the well-known oil drop method. Preparation of alumina-bound spheres generally involves dropping a mixture of molecular sieve, alumina sol, and gelling agent into an oil bath maintained at elevated temperatures. Alternatively, gelation of a silica hydrosol may be effected using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and an ammoniacal solution to further improve their physical characteristics.

An alternative shape for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of 30 to 50 wt-% being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

The resulting composites then preferably are washed and dried at a relatively low temperature of about 50° to 200° C. and subjected to a calcination procedure at a temperature of about 450° to 700° C. for a period of about 1 to about 20 hours.

Each of the catalysts may be subjected to steaming to tailor acid activity. The steaming may be effected at any stage of the treatment, but usually is carried out on a composite of zeolite and binder prior to incorporation of the platinum-group metal. Steaming conditions comprise a water concentration of about 5 to 100 volume-%, a pressure of about 100 kPa to 2 MPa, and a temperature between about 600° and 1200° C.; the steaming temperature is preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred. Alternatively or in addition to the steaming, the composite may be washed with one or more of a solution of ammonium nitrate, a mineral acid, and/or water. The washing may be effected at any stage of the preparation, and two or more stages of washing may be employed.

Tungsten is a preferred component of the first catalyst. Tungstate ions are incorporated into a catalytic composite, for example, by treatment with ammonium metatungstate in a concentration usually of about 0.1 to 20 mass-% tungsten and preferably from about 1 to 15 mass-% tungsten. Compounds such as metatungstic acid, sodium tungstate, ammonium tungstate, ammonium paratungstate, which are capable of forming tungstate ions upon calcining, may be employed as alternative sources. Preferably, ammonium metatungstate is employed to provide tungstate ions and form a solid strong acid catalyst. The tungstate content of a finished catalyst generally is in the range of about 0.5 to 30 mass-%, and preferably is from about 1 to 25 mass-% on an elemental basis. The tungstate composite is dried, preferably followed by calcination at a temperature of about 450° to 1000° C. particularly if the tungstanation is to be followed by incorporation of the platinum-group metal.

A platinum-group metal, including one or more of platinum, palladium, rhodium, ruthenium, osmium, and iridium, is an highly preferred component of each of the present catalyst composites. The preferred platinum-group metal is platinum. The relative platinum-group metal content of each of the first and second catalysts is a feature of the invention. The platinum-group metal, if present, generally comprises from about 0.01 to about 0.5 mass-%, preferably from about 0.5 to about 0.3 mass-% of the final first catalyst, calculated on an elemental basis; the second catalyst preferably comprises from about 0.01 to about 0.5 mass-%, preferably less than about 0.2 mass-% and especially from about 0.02 to about 0.08 mass-% of platinum-group metal on an elemental basis.

The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the sieve component and binder. Complexes of platinum-group metals which may be employed in impregnating solutions, co-extruded with the sieve and binder, or added by other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like. Preferably the platinum-group metal component is concentrated on the binder component of the catalyst by any method known in the art. One method of effecting this preferred metal distribution is by compositing the metal component with the binder prior to co-extruding the sieve and binder.

It is within the scope of the present invention that the present catalyst composites may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst of the present invention may contain a halogen component, comprising either fluorine, chlorine, bromine or iodine or mixtures thereof, with chlorine being preferred. Preferably, however, the catalyst contains no added halogen other than that associated with other catalyst components.

Each catalyst composite is dried at a temperature of about 100° to about 320° C. for a period of about 2 to about 24 or more hours and, usually, calcined at a temperature of 400° to about 650° C. in an air atmosphere for a period of about 0.1 to about 10 hours. If desired, an optional halogen component may be adjusted by including a halogen or halogen-containing compound in the air atmosphere.

The resultant calcined composites optimally are subjected to a substantially water-free reduction step to insure a uniform and finely divided dispersion of the specified metallic components. The reduction optionally may be effected in the process equipment of the present invention. Substantially pure and dry hydrogen (i.e., less than 20 vol. ppm $H_2O$) preferably is used as the reducing agent in this step. The reducing agent contacts the catalyst at conditions, including a temperature of about 200° to about 650° C. and for a period of about 0.5 to about 10 hours, effective to reduce substantially all of the Group VIII metal component to the metallic state. In some cases, the resulting reduced catalyst composite may also be beneficially subjected to presulfiding by a method known in the art to incorporate in the catalyst composite from about 0.05 to about 1.0 mass-% sulfur calculated on an elemental basis.

EXAMPLES

The following examples are presented only to illustrate certain specific embodiments of the invention, and should not be construed to limit the scope of the invention as set forth in the claims. There are many possible other variations, as those of ordinary skill in the art will recognize, within the spirit of the invention.

Samples of first catalysts directed to the conversion of nonaromatics in a $C_8$-aromatics mixture were prepared and tested comparatively in a pilot-plant.

Example I

A catalyst comprising extruded particles of MTW zeolite composited with alumina was prepared according to U.S. Pat. No. 7,525,008 B2. The particles were impregnated with a solution of chloroplatinic acid, dried, oxidized, reduced and sulfided to yield a catalyst containing about 0.05 mass-% platinum. This catalyst was designated Catalyst A.

Example II

A catalyst was prepared using the teachings of U.S. Pat. No. 6,143,941. An oil-dropped spherical catalyst of the reference comprising a zeolite and amorphous aluminum phosphate binder prepared according to Example I was ion-exchanged with ammonium sulfate (0.82 grams ammonium sulfate+10 grams deionized water per gram of support) at 60° C.; after decanting, the ion exchange was repeated and the resulting spheres were washed four times with 10 grams deionized water per gram of support. The spheres were dried at 120° C. for an hour and calcined at 350° C. and 550° C. in dry air for two hours. The spheres, having a sulfur content of about 0.7 mass-%, were impregnated with tetraamine platinum chloride to achieve a platinum content of about 0.04 mass-%, calcined at 525° C. in air with 3% steam for two hours and reduced at 425° C. in hydrogen for four hours. The resulting catalyst was designated Catalyst B.

Example III

Spherical alumina particles were prepared according to U.S. Pat. No. 2,620,314 and were metal-impregnated with ammonium metatungstate with added $NH_4OH$ at a pH of 9-10 to form a solid strong acid catalyst comprising about 10 mass-% tungsten. The composite was dried and calcined in dry air at 350° and 550° C. for three hours. The composite was impregnated with an aqueous solution of chloroplatinic acid and hydrochloric acid at pH of 9 to 10, dried at 350° C., ramped to 550° C. at 50° C./hour, purged with nitrogen, reduced in hydrogen at 565° C. for one hour and designated Catalyst C.

Example IV

Particles comprising an active layer of MTW zeolite on a $\frac{1}{16}$-inch gamma-alumina core were prepared according to U.S. Pat. No. 7,297,830, yielding a 150-micron layer of 10% MTW (40 $Si/Al_2$ ratio). The particles further were impregnated with ammonium metatungstate, with added $NH_4OH$ to a pH of 10, to form a solid strong acid catalyst comprising about 10 mass-% tungsten which was steamed and calcined in dry air at 350° and 550° C. for three hours. The composite was impregnated with an aqueous solution of chloroplatinic acid and hydrochloric acid at pH of 9 to 10 according to according to Example III of U.S. Pat. No. 7,297,830, yielding a catalyst in which over 90% of the platinum was concentrated in the outer zeolite layer. The composite was dried and calcined, followed by impregnation with an aqueous solution of chloroplatinic acid and hydrochloric acid according to according to Example III of U.S. Pat. No. 7,297,830, yielding a catalyst comprising 0.28 mass-% platinum in which over 90% of the platinum was concentrated in the outer zeolite layer. The particles were calcined and reduced to yield Catalyst D.

Example V

The four catalysts A-D were evaluated for conversion of nonaromatics in $C_8$ aromatics using a pilot-plant flow reactor processing a non-equilibrium $C_8$ aromatic feed having the following composition in mass-%:

| Catalysts Tested: | A and B | C and D |
|---|---|---|
| Composition, mass-%: | | |
| Ethylbenzene | 14.6 | 14.4 |
| Meta-xylene | 58.5 | 57.4 |
| Ortho-xylene | 24.4 | 24.3 |
| Cumene | 0.1 | 0.1 |
| n-nonane | 2.07 | 2.8 |
| 2-methyl octane | — | 0.51 |
| trimethylcyclohexanes | 0.27 | 0.49 |

Example VI

The four catalysts were tested at the following conditions:
12 hourly weight space velocity
4 molar hydrogen/hydrocarbon ratio
1-2 hours each at 385°/395°/405° C.

| Conversions were as follows in %: | A | B | C | D |
|---|---|---|---|---|
| n-nonane | 96 | 80 | 41 | 86 |
| 2-methyloctane | | | 16 | 12 |
| trimethylcyclohexanes | 88 | 23 | 90 | 85 |
| ethylbenzene | 30 | 58 | 8 | 11 |
| Net byproducts, mass-% | 10 | 4 | 6 | 7 |

The invention claimed is:

1. A process for the conversion of a hydrocarbon feed mixture comprising a major concentration of nonequilibrium $C_8$ aromatics and a minor concentration of nonaromatics by contacting the mixture with a dual-catalyst system comprising a first catalyst consisting of a tungsten component and a second catalyst comprising from about 0.01 to about 0.2 mass-% on an elemental basis of at least one platinum-group metal component at hydrocarbon-conversion conditions comprising a temperature of about 300° to about 550° C., a pressure of about 100 kPa to 5 MPa and a liquid hourly space velocity of about 0.5 to 50 $hr^{-1}$ with respect to the dual-catalyst system to obtain a converted product comprising a reduced concentration of ethylbenzene and a reduced concentration of nonaromatics than in the feed mixture.

2. The process of claim 1 wherein the concentration of nonaromatics is from about 0.5 to 10 mass-% of the feed mixture.

3. The process of claim 1 wherein the first catalyst comprises a layered sphere.

4. The process of claim 1 wherein the first and second catalysts are stacked sequentially.

5. The process of claim 1 wherein the catalyst system is a physical mixture of the first and second catalyst.

6. The process of claim 1 wherein the first and second catalysts are contained on the same catalyst particle.

7. The process of claim 6 wherein the first catalyst comprises a layer on the surface of the second catalyst.

8. A process for the conversion of a hydrocarbon feed mixture comprising a major concentration of nonequilibrium $C_8$ aromatics and a minor concentration of nonaromatics by contacting the mixture with a dual-catalyst system comprising a first catalyst consisting of a tungsten component and a second catalyst comprising from about 0.01 to about 0.2 mass-% on an elemental basis of at least one platinum-group metal component at hydrocarbon-conversion conditions comprising a temperature of about 300° to about 550° C., a pressure of about 100 kPa to 5 MPa and a liquid hourly space velocity of about 0.5 to 50 $hr^{-1}$ with respect to the dual-catalyst system to obtain a converted product comprising a higher proportion of at least one xylene isomer, a reduced concentration of ethylbenzene and a reduced concentration of nonaromatics than in the feed mixture.

9. The process of claim 8 wherein the concentration of nonaromatics is from about 0.5 to 10 mass-% of the feed mixture.

10. The process of claim 8 wherein the first catalyst comprises a layered sphere.

11. The process of claim 8 wherein the first and second catalysts are stacked sequentially.

12. The process of claim 8 wherein the catalyst system is a physical mixture of the first and second catalyst.

13. The process of claim 8 wherein the first and second catalysts are contained on the same catalyst particle.

14. The process of claim 8 wherein the first catalyst comprises a layer on the surface of the second catalyst.

* * * * *